United States Patent [19]

Yang

[11] Patent Number: 5,288,373

[45] Date of Patent: Feb. 22, 1994

[54] PROCESS OF REMOVING CYANIDE FROM WASTE WATER

[76] Inventor: Xinyu Yang, 23 Laoyang Zhuang, Chengbei, Zaoqiang County, Hebei 053100, China

[21] Appl. No.: 75,864

[22] Filed: Jun. 11, 1993

Related U.S. Application Data

[63] Continuation of Ser. No. 650,075, Feb. 4, 1991, abandoned.

[30] Foreign Application Priority Data

Mar. 15, 1990 [CN] China .................................. 90202759
Jun. 14, 1990 [CN] China .................................. 90104317

[51] Int. Cl.[5] .......................................... C02F 1/461
[52] U.S. Cl. .................................. 204/131; 204/149; 210/748
[58] Field of Search ................ 204/130, 131, 149; 210/748

[56] References Cited

U.S. PATENT DOCUMENTS

| | | | |
|---|---|---|---|
| 3,719,570 | 3/1973 | Lancy | 204/151 |
| 3,756,932 | 9/1973 | Zievers et al. | 204/149 |
| 3,788,967 | 1/1974 | Kawahata et al. | 204/277 |
| 3,900,377 | 8/1975 | Enns et al. | 204/149 |
| 3,970,531 | 7/1976 | Recht | 204/149 |
| 4,024,037 | 5/1977 | Bishop et al. | 204/149 |
| 4,029,557 | 6/1977 | Christensen et al. | 204/149 |
| 4,131,526 | 12/1978 | Moeglich | 204/149 |
| 4,226,685 | 10/1980 | Portal et al. | 204/105 R |
| 4,417,963 | 11/1983 | Janné | 204/130/ |
| 4,761,208 | 8/1988 | Gram et al. | 204/95 |
| 5,022,974 | 6/1991 | Häiälä | 204/275/ |

FOREIGN PATENT DOCUMENTS

| | | |
|---|---|---|
| 1025282 | 4/1966 | European Pat. Off. . |
| 1382540 | 2/1975 | European Pat. Off. . |
| 1433858 | 4/1976 | European Pat. Off. . |
| 1505361 | 2/1978 | European Pat. Off. . |
| 49-120463 | 11/1974 | Japan . |

OTHER PUBLICATIONS

*Metalloberflache*, "Entgiftung von Zyanidabwässern aus Galvanisierungswerkstätten mit Hilfe der kontinuierlichen elektrolytischen Chlorierung", Eigenschaften et al., vol. 8, pp. 225–231, 1969.

*Galvanotechnik*, "Entgiftung cyanidischer Abwässer", Knorre, vol. 66, No. 5, pp. 374–383, 1975.

*Primary Examiner*—John Niebling
*Assistant Examiner*—Arun S. Phasge
*Attorney, Agent, or Firm*—Kinney & Lange

[57] ABSTRACT

A process for removing cyanide from liquid waste by electrolysis is disclosed. The method includes combining waste water and NaCl to an electrolyser cell, the cell having positive and negative electrode plates. The NaCl concentration in the cell is maintained at about 180 g/l. HCl and NaOH are added to maintain the pH at about 10.5. The liquids are agitated, and a current is applied to the electrode plates. The cyanide is decomposed, and the heavy metals are separated out. The waste gasses are sent through a purifying tower where $CO_2$ and $N_2$ are released. A decyanation apparatus comprising an electrolyser and a gas purifier is also disclosed.

8 Claims, 5 Drawing Sheets

PROCESS OF REMOVING CYANIDE FROM WASTE WATER

This is a continuation of application Ser. No. 07/650,075 filed on Feb. 4, 1991, abandoned as of the date of this application.

TECHNICAL FIELD

The present invention relates to the purification of water, particularly to an apparatus for removing cyanide from liquid waste a decyanation apparatus and a process using the same for purifying polluted water.

BACKGROUND OF THE INVENTION

It is well known that hypertoxic cyanides exist in liquid waste from existing production processes of ore dressing, metallurgy, coking and electroplating etc. and methods universally adopted for removing cyanide such as ionic exchange, ozonization or direct electrolytic oxidation are not efficient. For example, in electrolytic oxidiation the current efficiency is not stable, therefore harmful gases are generated in the process and the processing cost is high. During the operation of the niobium anode cyanide processor, explosive gases such as hydrogen and chloramine as well as toxic gases such a nitrogen trichloride, cyanhydrin and chloride acid escaped may cause secondary pollution. In alkaline chlorine process, a chloric oxidant (chlorine, liquid chlorine sodium subchlorate, or bleaching power etc.) is added to the cyanide containing water so as to oxidize and decompose cyanides under alkaline condition. Since availibe chlorine may degrade during the storage of chloric oxidants, it reacts chemically with cyanic ions in the process, generating harmful gases such as cyanic acid and cyanogen chloride. In addition, chloric oxidants are easy to leak out during the transportation, therefore, secondary pollution might be caused. The chlorinecyanogen equivalent weight is not easy to control in the process, which may produce excessive chlorine or cause the cyanogen content to exceed discharge standard. Meanwhile the cost is high.

Ionic exchange is usually used in the desalination of drinking water, and the processing of heavy metal ions and radioactive elements. It is effective in processing liquid waste containing less than 50 PPM of cyanogen and not suitable to process liquid waste containing more than 200 PPM of cyanogen.

SUMMARY OF THE INVENTION

The object of the present invention is to provide a decyanation apparatus which can remove hypertoxic cyanide from the liquid industrial waste and therefore solve the problems which existed in the prior art apparatus.

Another object of the present invention is to provide a novel process for purifying liquid industrial waste using said apparatus in combination with the principles of electrochemical reaction so as to remove cyanide through electrolytic purification. The gases exhausted from the process are repurified, thus the problem of secondary pollution is solved.

The objects of the present invention are realized in a manner that three storage tanks containing HCl, NaOH and NaCl respectively supply said materials via electromagnetic valves and pipes to an electrolyser cell with their amount controlled by a flowmeter; the liquid waste is pumped into the cell of an electrolyser from a water collecting sump; the pH value in the electrolyser cell is controlled and displayed on a controlling board via a pH sensor and an oxidation-reduction potentiometer (ORP) provided within the electrolyser; a fan outside the electrolyser blows air into the electrolyser cell for stirring which is further promoted by a three-dimentional eddy current generated by spray nozzles installed vertically and horizontally in the electrolyser; a set of electrode plates provided within the electrolyser cell reverse polarities under the control of a inverter; the CN bond of the cyanide is completely destroyed in the electrolysis and the gases exhausted from the electrolyser are sent to a purifying tower by a fan; there stored within the tower liquid alkali which is sprinkled by nozzles of a sprinkling unit; the gases sprinkled with liquid alkali pass through a PN filler (Paul ring) layer in the middle section of the tower and are transformed into $CO_2$ and $N_2$ which are then exhausted. There is no secondary pollution casused by gases that have been processed thus and so.

DETAILED DESCRIPTION OF THE PREFERRED EMBODIMENT

Figure 1:
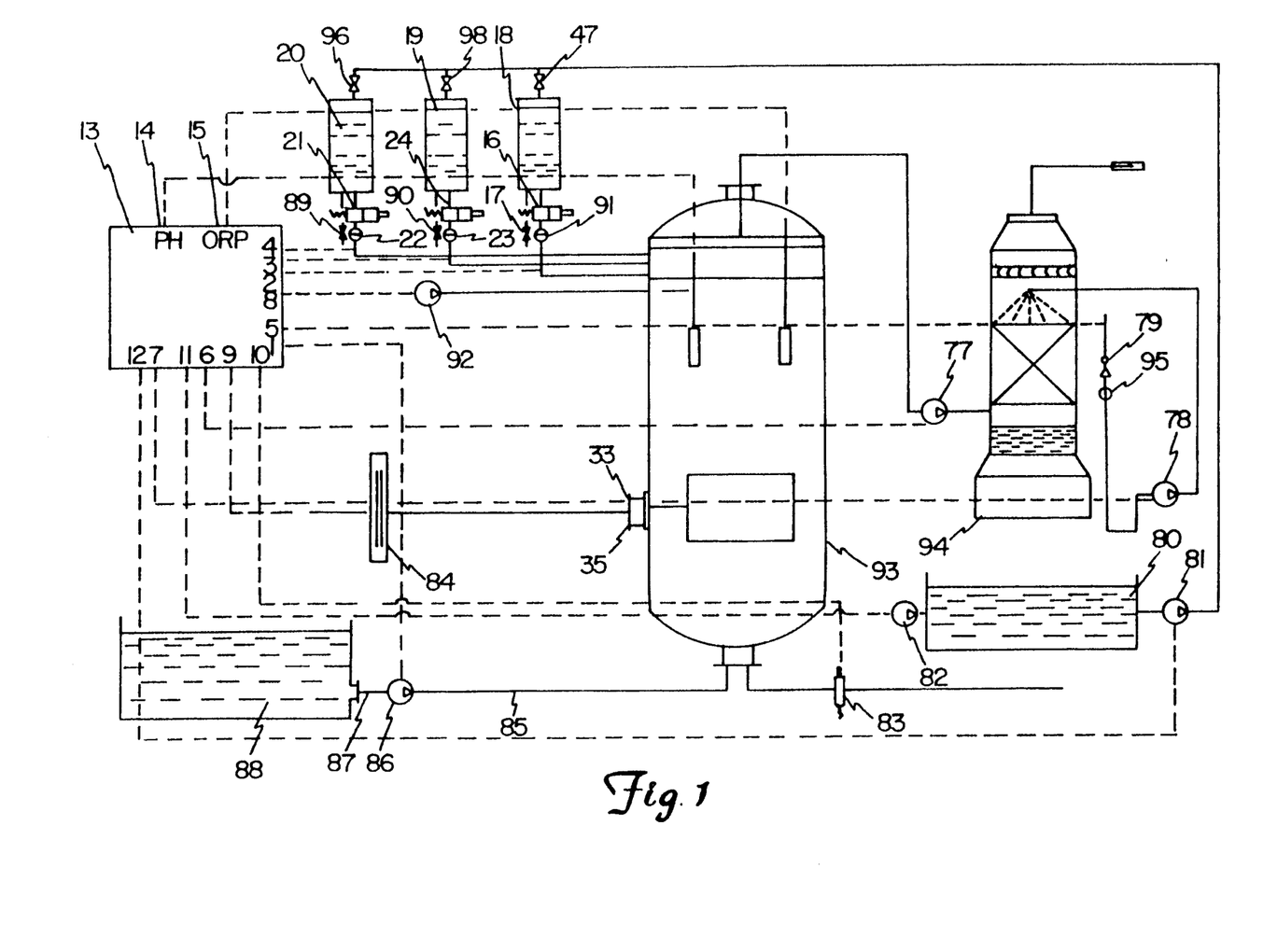
FIG. 1 is an embodiment of the decyanation apparatus according to the present invention.

FIG. 1 shows an embodiment of the decyanation apparatus according to the present invention.

A pH acidimeter (14) and an oxidation-reduction potentiometer (ORP) (15) are provided on a control board (13). A set of 6 keys on the right side of the board functions as follows: key (1) is connected to the inlet pump of the electrolyser (93) and controls the operation of the pump; key (2) is connected to an electromagnetic valve (16) and a flowmeter of a hydrochloric acid tank (18); key (3) is connected to an electromagnetic valve (24) and a flowmeter of a alkali tank (19); key (4) is connected to a electromagnetic valve (21) and a flowmeter of salt tank (20); the three keys (2, 3, 4), according to the display of pH acidimeter (14), control the addition of materials in the acid alkali and salt tanks (18, 19, 20) into the cell of the electrolyser (93) so as to match the pH value with a given valve; key (5) is connected to an electromagnetic valve (79) and a flowmeter (95) for controlling the flow of liquid alkali into the purifying tower; key (8) is connected to a fan of the electrolyser (93) and controls the fan to blow air into the electrolyser for stirring. Another set of 6 keys on the lower part of the control board is provided, among them, key (10) connected to the discharge electromagnetic valve (83) on a flange below the electrolyser (93), controls the discharge of water; silicon rectifying switch (9) controls the thyristor (84) having a phase-inverter, the output terminal of which is connected to the positive and negative electrode wiring board (33, 35) of the electrolyser (93) to reverse the polarity of the electrodes at regular intervals so as to speed up electrolysis; key (6) is connected to a fan (77) in the passage between electrolyser (93) and the purifying tower, for controlling the fan to blow waste gases exhausted from the electrolyser (93) to the purifying tower (94) and maintain a continued purifying action; key (11) is connected to a fan (82) for agent tank (80) to control the fan to give a stir in the agent tank (80); key (7) is connected to an alkali pump (78) of the purifying tower (94) and controls the pump to pump liquid alkali from the purifying tower (94) into a sprinkling pipe (72) on the upper section of the purifying tower, the liquid alkali is then sprinkled via a number of nozzles, generating a purifying action on the waste gases filtered by a filtering layer; key (12) is connected to a agent pump (81) for tank (80) to control the pump to pump off acid, alkali and salt in tank (80).

Figure 2:
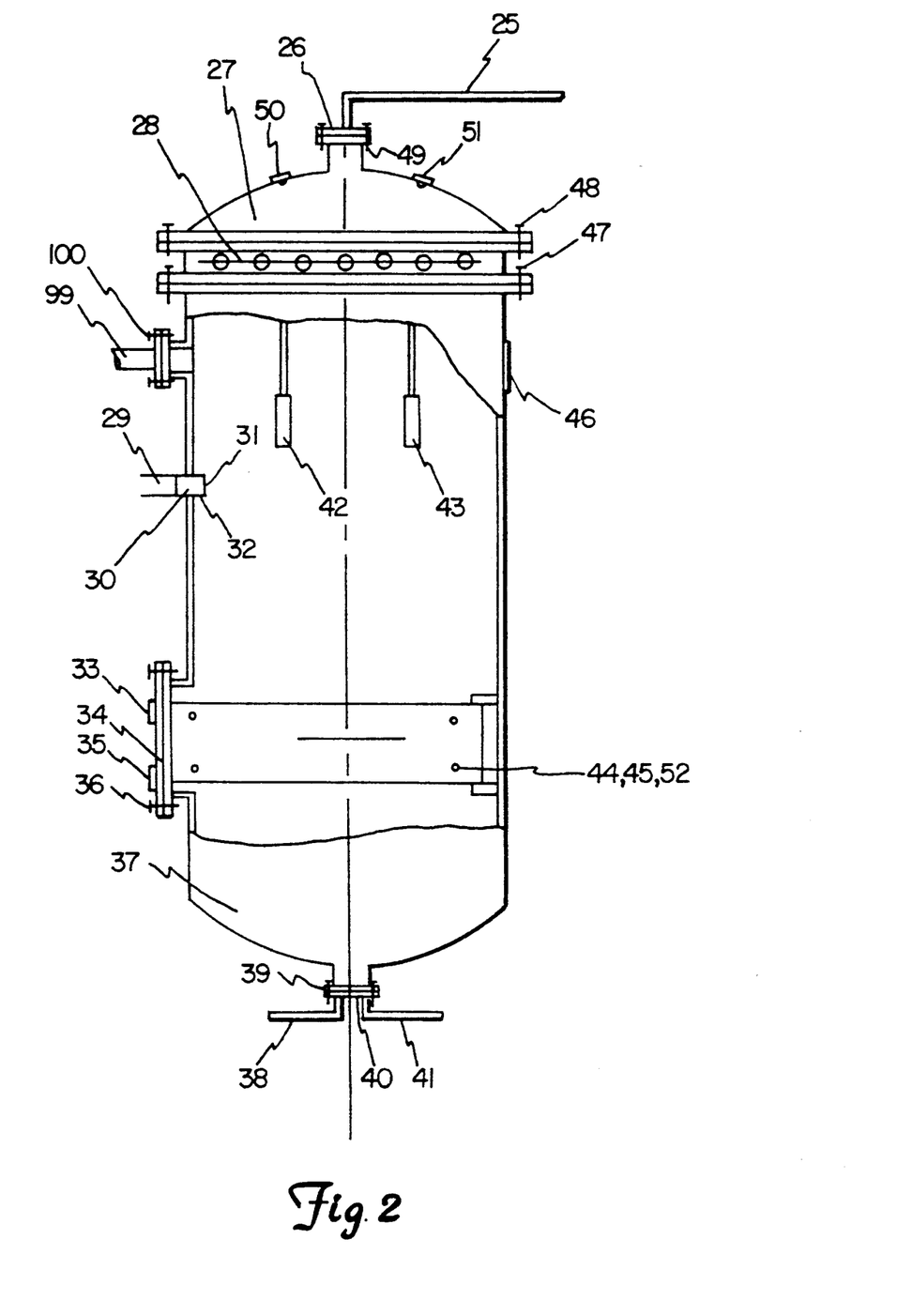
FIG. 2 is the front view of an embodiment of the electrolyser.

In FIG. 2 the electrolyser of the apparatus according to the present invention comprises an electrolyser cover (87), a water-gas separating member (28), a cylindrical body (27) and a set of electrode plates etc. Electrolyser cover (27) is a pot-shaped covering member with its central top extended upward forming a flange which is connected with another flange (26) by bolts (49) or other means. Flange (26) is connected to an exhaust pipe (25). A connection socket (50) for a pH sensor and a connection socket 51 for a ORP sensor are mounted in opposition to each other on cover (27).

On the cylindrical body (37), a blower (30) is provided between the body and an air inlet pipe (29) to the body, and connected with a plurality of horizontal and vertical blowing nozzles (31, 32) inside the body. A positive wiring means (33) and a negative wiring means (35) are fixed on a flange (34) by means of screws or the like. Flange (34) is connected fixedly with a flange projected outward from the body and having an opening through which a set of electrode plates defining an anode and a cathode is inserted into the lower part of the body defining a electrolyser cell. The electrode plates are connected fixedly to each other by means of bolts (44), nuts (45) and washers (52) all painted with a layer of anticorrosive PTFE. The electrode plate set is supported by a frame connected integrally with the body and projected inward in the body. The body has a contour at its bottom similar to cover (27). i.e. a pot-shaped contour with its central part projected downwardly forming a flange connected with a flange (40) by bolts (39). A liquid waste inlet pipe (38) and a discharge pipe (41) are connected to extend through flange (40) in opposition to each other. A pH acidimeter (42) and an ORP sensor (43) are disposed within the body above the blowing nozzles. A floating-ball fluviograph is installed on the body to control the liquid level in the body.

Figure 3:
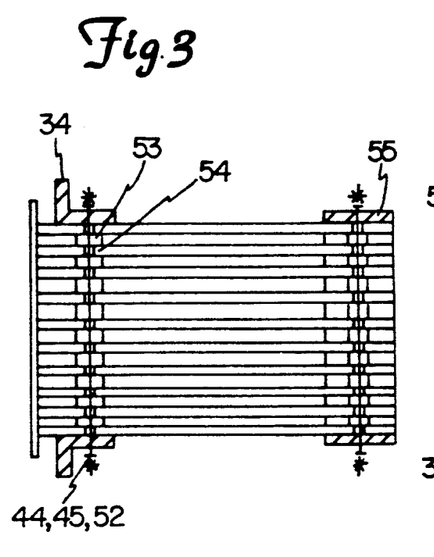
FIG. 3 is the front view of an embodiment of the electrode plate set.

FIG. 3 is the front view of the electrode plates set. The positive plates (56) (anode) and the negative plates (57) (cathode) are equal in number and arranged positive alternating with negative with spacings between each pair of plates being preferably 5 mm and filled with insulation blocks (53). Each electrode plate has two holes provided at two ends respectively; within each hole an insulating ring (54) is placed. Each insulation block (53) also has a central hole so that the connecting bolts (44) can be inserted through which and the hole at the end of the plate to fix plates (56, 57) onto a supporting frame (55) and wiring flanges (34). In order to avoid corrosion, bolts (44), nuts (45) and washers (52) are preferably made of stainless steel or other sort of steel painted with PTFE.

Figure 4:
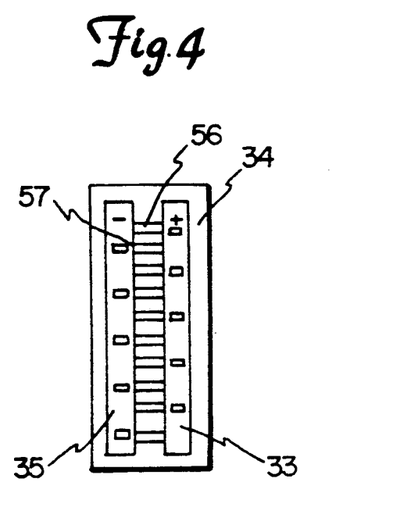
FIG. 4 is the contour of an electrode plate of the electrode plate sets in FIG. 3.
Figure 5:
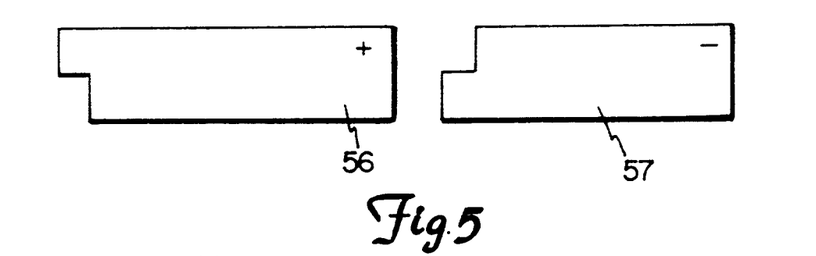
FIG. 5 is an illustration showing the shape of the electrode plates.

FIG. 4 is the lateral view of the electrode plate set. Two rectangular copper plates (one as positive and the other as negative) are spaced apart in opposition to each other. On each of which openings equal in number to the positive or negative plates are provided to receive positive or negative plates in a manner that positive electrode plates (56) are inserted fixedly into the openings on positive copper plate and negative electrode plates into negative copper plate. The electrode plates are cut to the shape shown in FIG. 5 so that the possibility of coming into contact with two copper plates by an electrode plate is eliminated. With the action of a phase-inverter, the polarities of the electrode plates reverse in regular intervals, thus the inactivation of electrodes is effectively avoided while the bath voltage is stabilized.

Figure 6:
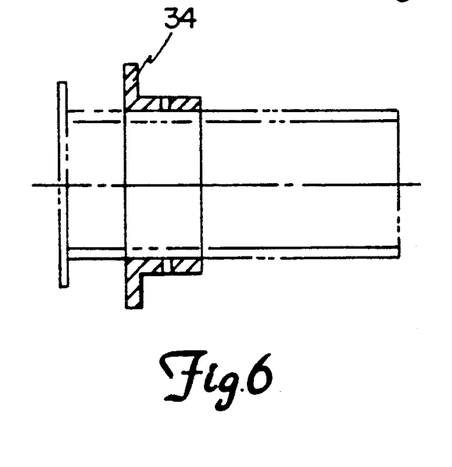
FIG. 6 is the sectional view of the wiring flange for the electrode plate set.

FIG. 6 is the sectional view of the wiring flange (34). Flange (34) is shaped into a rectangular sleeve so that the electrode plate set can be placed therein. A pair of round holes perpendicular to the rectangular opening of the sleeve and in opposition to each other on the sleeve are also provided on the flange to fix the electrode plates (56, 57) with insulation blocks therebetween onto the flange.

Figure 7:
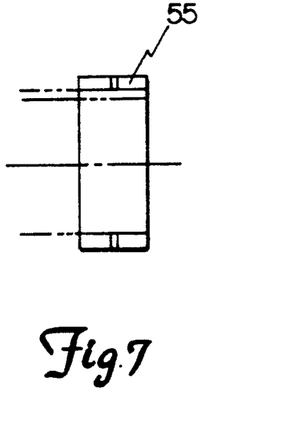
FIG. 7 is the sectional view of the supporting frame of the electrode plate set.

FIG. 7 is the sectional view of the supporting frame (55). Supporting frame (55) is also in the form of a rectangular sleeve into which the electrode plate set is placed. At its upper and lower ends, holes are provided perpendicular to the rectangular opening of the sleeve so as to supportedly fix the electrode plates with insulation blocks there between into the frame.

Figure 11:
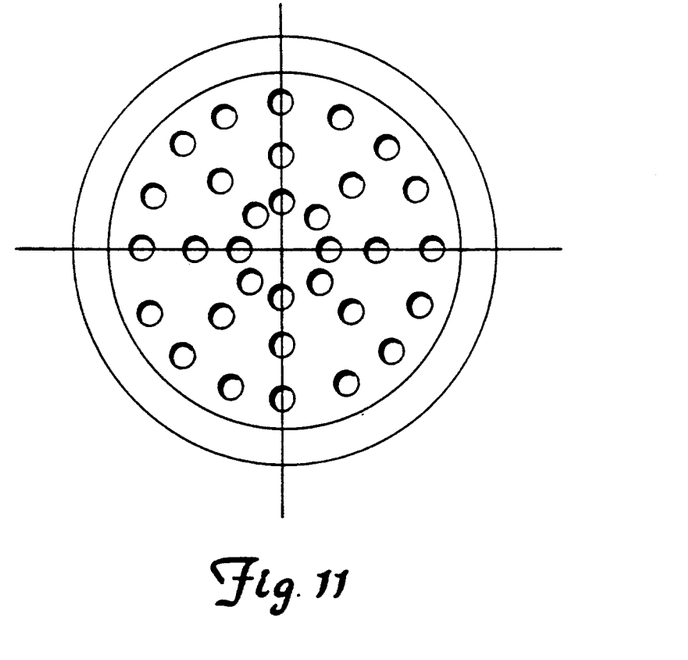
FIG. 11 is the top view of the water-gas separating member of the purifying tower.

Now refer to FIG. 11. A water-gas separating member (28) is provided between the cover (27) and the body 37 of the electrolyser, which is made up of two perforated plastic plates sandwiched therebetween a thin layer of fiber material for water-gas separation. A plurality of ventilating holes are provided on the side wall of the member, thus the concentration of waste gases may be diluted during air exhaust and the possible explosion ignited by high density hydrogen and backflow caused by the negative pressure owing to the insufficient amount of air from the blower are prevented.

Figure 8:
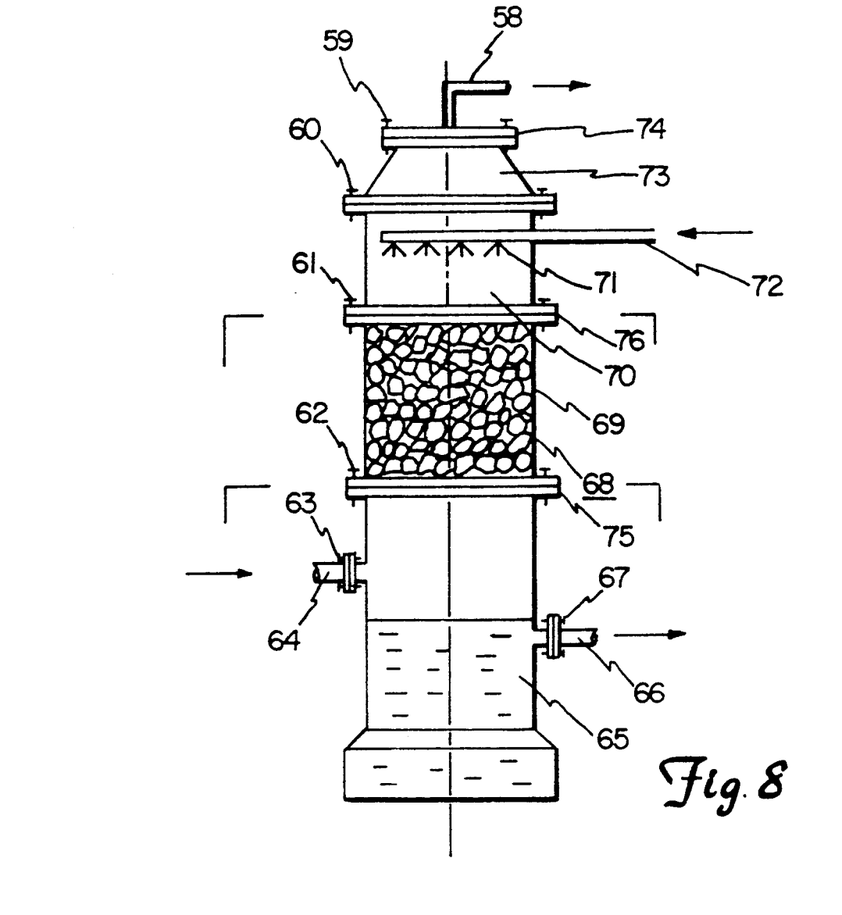
FIG. 8 is the front view of the purifying tower.

FIG. 8 is the front view of the waste gas purifying tower (94). Purifying tower (94) is a cylindrical body constructed of three sections. The upper section is connected at is top with a taper cover forming a water-gas separating member (73) of the purifying tower; a flange formed thereon is connected with a flange (74) by bolts (59); through the central portion of flange (74) an exhaust pipe (58) for exhausting purified nontoxic gases $CO_2$ and $N_2$ is hermetically inserted into the body. A liquid alkaline sprinkling pipe (72) with 4-5 sprinkling nozzles (71) is provided within the upper section of the body by extending the same hermetically therethrough, so that a sprinkling chamber (70) is formed. The middle section of the cylindrical body is filled with polyhedral PN particles (Paul Ring) (68) forming a gas-liquid reaction chamber (69) for changing the liquid phase of the waste gases and hydrolyzing and oxidizing the waste gases. A flange-like porous lower supporting plate (75) is provided between the lower section and the middle section, a similar upper supporting plate (76) is installed between the middle section and upper section. The lower section of the cylindrical body is divided into two parts; the upper part has a flange projected outwardly thereform which is connected with a waste gas inlet pipe (64) having a flange at its end; and the lower part forms a liquid alkali storage tank (65) which also has a flange projected outwardly therefrom and connected a pipe (66) to a liguid alkali pump, the bottom of the liquid alkali storage tank (65) is taper shaped to increase the stability and capacity of the tower.

Figure 9:
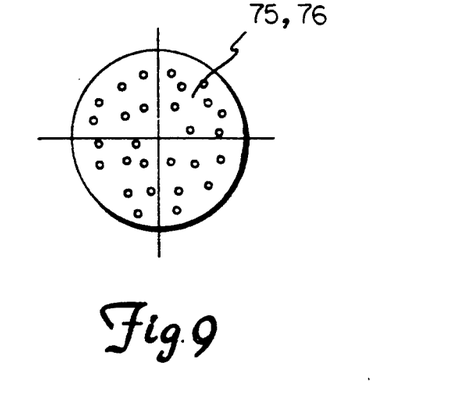
FIG. 9 is the schematic diagram of the upper and lower supporting plates.
Figure 10:
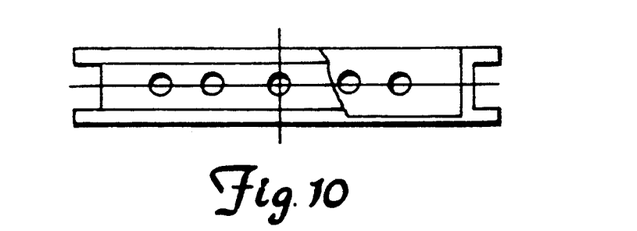
FIG. 10 is the front view of an embodiment of the water-gas separating member of the purifying tower.

FIG. 9 is the schematic diagram of the upper and lower supporting plates. The upper and lower supporting plates (76, 75) are in the form of disc with a plurality of apertures for filtration.

The purifying process of the present invention is now described.

Firstly, the liquid waste in a precipitating pool is pumped into the cell of electrolyser (93); HCl (30%), NaOH (16%) and NaCl are piped from three storage tanks via electromagnetic valves into the electrolyser cell in which the pH value of the liquid waste is adjusted to 10.5 according to the display of acidimeter (14) by adding acid or alkali into the cell. The adoption of pH acidimeter for automatically monitoring, controlling and adjusting the pH valve of the liquid waste in the electrolyser cell shortens the reaction process, increases current efficiency and reduces the operation cost. Next, NaCl of 180 g/l is added into the electrolyser cell under the control of a electromagnetic valve, a flowmeter and a timer in a manner that the Nacl/liquid waste is controlled to 0.15 g/l~3 g/l according to the concentration of the liquid waste.

Then air is blown into the electrolyser cell by blower (30) to give a stir to the liquid therein. The introduction of air-stir in the electrolyser cell prevents the precipitation of metal cyanide and the formation of flocculus substance which may adsorb cyanic ions, hence reduces concentration difference so that the undissolved chlorine accelerates the decomposition of CN. Liquid NaOH is piped from the alkali tank via electromagnetic valve (24) into the storage tank within the purifuing tower and then sprinkled onto the waste gases to be purified. The waste gas then passes through a layer of PN fillers. The main reactions in the purifying tower are $NaOH + HCN \rightarrow NaCN + H_2O$ $CN^- + Cl_2 + 2OH^- \rightarrow CNO^- + 2Cl + H_2O$ $2CHO^- + 3CLO^- + H_2O \rightarrow CO_2 \uparrow + N_2 \uparrow + ON^- + 3Cl$ $CNCl + 2NaOH \rightarrow NaCNO + NaCl + H_2O$ $2NaCNO + 3NaCLO + H_2O \rightarrow 2CO_2 \uparrow + N_2 \uparrow + 2NaOH + 3NaCl.$ The liquid waste containing cyanide is electrolytically oxidized. The waste gas produced from electrolysis is decomposed and purified in the purifying tower, where the CN bond is destroyed completely, and the metal ions are separated out on the negative plates.

The reactions on the anode in the electrolyser cell are $CN^- + 2OH^- - 2e \rightarrow CNO^- + H_2O$ $2CHO^- + 4OH^- - 6e \rightarrow 2CO_2 \uparrow + N_2 \uparrow + 2H_2O$ $4OH^- - 4e \rightarrow 2H_2O + O_2 \uparrow$ The reaction on the cathode is $2H^+ + 2e \rightarrow H_2 \uparrow$ with heavy metals reduced and separated out; the secondary reaction is $CNO^- + 2H_2O \rightarrow NH_4 + CO_3^{2-}$ In order to accelerate the oxidization and decomposition of cyanide in the electrolyser cell, NaCl is added. The reaction on the anode is $Cl - e \rightarrow (Cl)$ and secondary reactions are $2Cl - 2e \rightarrow Cl_2$ $2OH^- + Cl_2 \rightarrow OCl^- + Cl^- + H_2O$ $CN^- + OCl^- + 2H_2O \rightarrow CNCl + 2OH^-$ $CNCl + 2OH^- \rightarrow CNO^- + Cl^- + H_2O$ $2CNO^- + 3OCl + H_2O \rightarrow 2CO_2 \uparrow + N_2 \uparrow + 3Cl^- + H_2O$ and $HOCl \rightarrow HCl + (O)$ To overcome the problems which existed in existing processes of decyanide by electrolysis, i.e. instability of current efficiency, generation of harmful gases and high processing cost, experiments have been made by the inventor on the condition of electrolytical oxidization, current efficiency and the correlation among the related quantities in the process. The prerequisite for a solution to the existing problems is found to be the materal of electrode. Hence, on the basis of the research on titanium electrode by Dt-Nora (Italy), Damond (USA), ICI (UK), a new electrode DSA5 is developed, with which high current density electrolysis can be realized and the separating-out of nascent oxygen and nascent chlorine is promoted. Furthermore, the current efficiency is increased.

The apparatus according to the present invention is provided with insoluble electrodes of the same material in a manner that the positive and negative electrodes are equal in number and arranged in an assembly with small spacings therebetween. The electrodes used in the apparatus according to the present invention are capable of resisting high-density current and changing polarities automatically. Due to the salt adhered onto the negative plates caused by the products on the electrodes, the deposit of calcium and magnesium ions on negative electrode, the concentration of products and electrolyte in the solution, the electrodes exhibit different overpotentials for different Cl and $H^+$, hence the bath resistance in the electrolyser cell is increased resulting in boosting of bath voltage and reduction of current efficiency. The adoption of phase-reversion effectively prevents the inactivation of electrodes, increases the conductivity, reduces voltage drop, therefore stabilizes the bath voltage and maintains a low overpotential for Cl (a low EMF for separating out chnorine). In the process, no sludge is procuded and secondary pollution is prevented accordingly.

The adoption of high density current (55 A/dm²), small spacing between electrodes and phase-reversion at regular intervals (every 3-8 minutes) facilitates decomposition of cyanide at both positive and negative electrodes; while the addition of sodium chloride (0.5–3 g/l) results in the generation of sodium subchlorate with remaining cyanogen being oxidized by chlorine at a certain pH value (10.5).

During the electrolysis, CN is continually destroyed and the complexing equilibrium of metal cyanide complexes is destroyed forming insoluble metal cyanide which then precipitates, and at the same time forming flocculent substance which adsorbs a few cyanogen ions. The formation of insoluble metal cyanide and flocculus substance prevents oxidization of cyanogen by available chlorine. To solve this problem air-stirring is introduced, which results in the reduction of differential concentration and accelerates decomposition of CN in combination with undissolved chlorine. Comparing with mechanical stirring, air-stirring is advantageous to the dissociation of cyanide. In the electrolyser cell, sodium subchlorate and chlorine are generated because of the addition of NaCl thereinto. The reaction is:

$$NaCN + NaClO \rightarrow NaOCN + NaCl$$

$$NaCN + Cl_2 + 2NaOH \rightarrow NaOCN + 2NaCl + H_2O$$

It has been found through experiments that the reaction finishes instantaneously when pH>12 and the critical pH value is 10.5, but the primary product is hypertoxic cyanogen chloride no matter how high the pH value is $$NaCN + NaClO + H_2O \rightarrow CNCl_2 + 2NaOH$$

For pH<10.5, the following hydrolytic process occurs:

$$CNCl + 2NaOH \rightarrow NaCl + NaCNO + H_2O$$

while NaOCN (cyanate) is completely oxidized into nitrogen, i.e.

$$2NaOCN + 3Cl_2 + 6NaOH \rightarrow 2NaHCO_3 + N_2 \uparrow + 6NaCl + 2H_2O$$

where the critical pH is just the same as that in the process of cyanide transforming into cyanate, i.e. 10.5.

The oxide content in the process of reaction varies from a few milligrams per liter up to thousands of milligrams per liter with industries. Therefore, a oxidizing reducing potentiometer (ORP) is employed to automatically monitor the oxide content so that electrolysis can be carried out without testing the oxygen content in the liquid waste separately. ORP is also used to monitor the equivalent potential of chlorine and cyanogen. As the reading of ORP reaches 350 mv (terminal potential) the liquid waste that has been purified is discharged. This significantly simplifies the procedure of lab testing of the content of chlorine and cyanogen and the feeding metering of chlorine and cyanogen and feeding metering of the reagents.

The apparatus according to the present invention is capable of treating 0.1–1000 tons of liquid waste a day with the concentration of the water to be purified being 1–8000 mg/l.

I claim:

1. A process for removing cyanide from liquid waste by electrolysis comprising the steps of:
    adding liquid waste containing cyanide to an electrolyser cell;
    maintaining a pH of said liquid waste at about 10.5;
    adding NaCl into said electrolyser cell in a manner that a NaCl/liquid waste radio is controlled to about 0.5–3 g/l;
    agitating the liquid in said electrolyser cell;
    applying a high density current to a set of positive and negative electrode plates defining an anode and a cathode respectively in said electrolyser cell;
    monitoring an equivalent potential of chlorine and cyanogen of the liquid in the electrolyser cell;
    discharging treated liquid from the electrolyser cell when a potential of the liquid approaches a selected value; and
    conveying waste gases consisting essentially of HCN and CNCl produced in the electrolysis to a purifying tower and purifying said gases therein.

2. The process of claim 1 wherein HCl is added to maintain the pH of the liquid waste at about 10.5, wherein the HCl is added in a liquid form, and the liquid comprises about 30% HCL.

3. The process of claim 1 wherein NaOH added to maintain the pH of the liquid waste at about 10.5, wherein the NaOH is in a liquid form, and the liquid comprises about 16% NaOH.

4. The process of claim 1 wherein the NaCl added is in a liquid form, and the liquid comprises about 180 g/l NaCl.

5. The process of claim 1 wherein the liquid in said electrolyser cell is agitated by means of air.

6. The process of claim 1 wherein the current applied to the electrodes is low tension and high density, having a value of about 55 A/dm$_2$.

7. The process of claim 1 wherein a group of reactions at the anode comprise:

$$CN^- + 2(OH)^- - 2e \rightarrow CNO^- + H_2O$$

$$2CHO^- + 4(OH)^- - 6e \rightarrow 2CO_2 + N_2 + 2H_2O$$

$$4(OH)^- - 4e \rightarrow 2H_2O + O_2$$

wherein heavy metals are separated out on a cathode and hydrogen is released, producing waste gases; wherein a secondary reaction is:

$$CNO^- + 2H_2O \rightarrow NH_4 + CO_3^{2-}$$

wherein waste gases elected from the group consisting essentially of HCN and CNCl are produced and conveyed to a purifying tower, wherein NaOH in liquid form is added to the purifying tower, wherein the following reactions take place:

$$NaOH + HCN \rightarrow NaCN + H_2O$$

$$CN^- + Cl_2 + 2OH^- \rightarrow CNO^- + 2Cl^- + H_2O$$

$$2CNO^- + 3ClO^- + H_2O \rightarrow CO_2 + N_2 + ON^- + 3Cl^-$$

$$CNCl + 2NaOH \rightarrow NaCNO + NaCl + H_2O$$

$$2NaCNO + 3NaClO + H_2O \rightarrow 2CO_2 + N_2 + 2NaOH + 3NaCl$$

wherein said waste gases existing in the purifying tower pass through a layer of pH fillers, wherein said waste gases are converted to CO$_2$ and N$_2$ exhaust gas.

8. The process of claim 1 wherein the selected potential is about 350 mv.

* * * * *

UNITED STATES PATENT AND TRADEMARK OFFICE
CERTIFICATE OF CORRECTION

PATENT NO. : 5,288,373

DATED : February 22, 1994

INVENTOR(S) : XINYU YANG

It is certified that error appears in the above-identified patent and that said Letters Patent is hereby corrected as shown below:

On the Title Page, in the [56] References Cited Section, under U.S. PATENT DOCUMENTS, delete:

4,417,963  11/1983  Janné 204......130/

5,022,974  6/1991  Häiälä 204.....275/ insert:

4,417,963  11/1983  Janné..........204/130

5,022,974  6/1991  Häiälä.........204/275

On the Title Page, in the [56] References Cited Section, under FOREIGN PATENT DOCUMENTS, delete:

1025282  4/1966  European Patent Off. .

1382540  2/1975  European Patent Off. .

1433858  4/1976  European Patent Off. .

1505361  2/1978  European Patent Off. .

UNITED STATES PATENT AND TRADEMARK OFFICE
CERTIFICATE OF CORRECTION

PATENT NO. : 5,288,373
DATED : February 22, 1994
INVENTOR(S) : XINYU YANG

It is certified that error appears in the above-indentified patent and that said Letters Patent is hereby corrected as shown below:

insert:

1025282 4/1966 United Kingdom. .
      1382540 2/1975 United Kingdom. .
      1433858 4/1976 United Kingdom. .
      1505361 2/1978 United Kingdon. .

Signed and Sealed this

Nineteenth Day of July, 1994

Attest:

BRUCE LEHMAN

*Attesting Officer*     *Commissioner of Patents and Trademarks*